US006471680B1

(12) United States Patent
Cawood

(10) Patent No.: US 6,471,680 B1
(45) Date of Patent: Oct. 29, 2002

(54) URINE BAG AND SELF-RETRACTING DRAIN TUBE THEREFOR

(75) Inventor: Charles David Cawood, Houston, TX (US)

(73) Assignee: Cawood Family Limited Partnership, Houston, TX (US)

( * ) Notice: Subject to any disclaimer, the term of this patent is extended or adjusted under 35 U.S.C. 154(b) by 0 days.

(21) Appl. No.: 09/499,841

(22) Filed: Feb. 7, 2000

Related U.S. Application Data

(63) Continuation-in-part of application No. 09/229,799, filed on Jan. 13, 1999, now Pat. No. 6,045,542.

(51) Int. Cl.[7] .................................................. A61B 1/00
(52) U.S. Cl. ...................................... 604/327; 604/349
(58) Field of Search ................................ 604/322, 324, 604/327, 328, 329, 345, 349, 512, 544; 128/DIG. 24

(56) References Cited

U.S. PATENT DOCUMENTS

| 2,612,895 | A | | 10/1952 | Magee | 604/327 |
| 2,900,979 | A | | 8/1959 | Bishop | 604/327 |
| 3,672,372 | A | | 6/1972 | Heimlich | 604/544 |
| 3,721,243 | A | | 3/1973 | Hesterman et al. | |
| 3,897,785 | A | | 8/1975 | Barto, Jr. | 604/327 |
| 3,943,929 | A | | 3/1976 | Patel | 604/544 |
| 4,224,610 | A | | 9/1980 | Quinby | |
| 4,230,115 | A | | 10/1980 | Walz et al. | |
| 4,306,976 | A | | 12/1981 | Bazzato | |
| 4,449,971 | A | * | 5/1984 | Cawood | 604/328 |
| 4,581,763 | A | | 4/1986 | Olsen | |
| 5,234,420 | A | * | 8/1993 | Horton et al. | 604/345 |
| 5,496,300 | A | * | 3/1996 | Hirsch et al. | 604/327 |
| 5,531,724 | A | * | 7/1996 | Young et al. | 604/327 |

FOREIGN PATENT DOCUMENTS

DE          3722-251 A          1/1989

* cited by examiner

Primary Examiner—Anhtuan T. Nguyen
(74) Attorney, Agent, or Firm—James L. Jackson; Andrews, Kurth, Mayor, Day & Caldwell, LLP

(57) ABSTRACT

A urine collection bag includes an improvement in the form of an extendable drain tube that is normally retracted and retained in flat coiled condition against the front wall of the bag. The tube is biased into its coiled condition by the elastic memory of the thermoplastic material from which it is formed and, in a preferred embodiment, the flat coil is oval-shaped with its major axis extending generally vertically when the bag is worn. A retention strap attached to the front wall of the bag serves to hold the drain tube in its coiled condition against the bag's front wall.

6 Claims, 1 Drawing Sheet

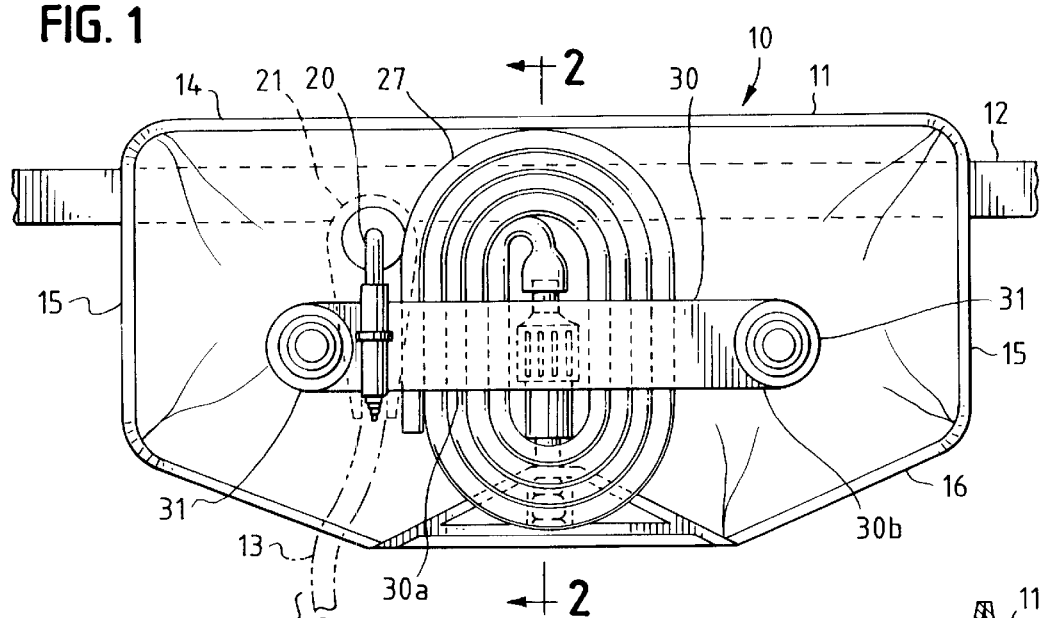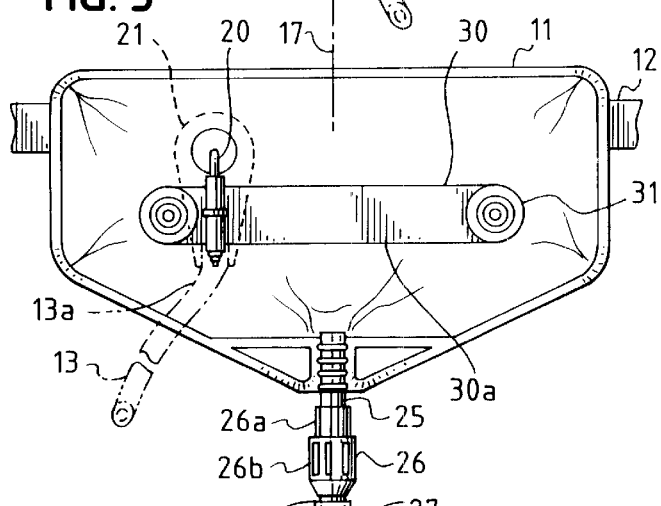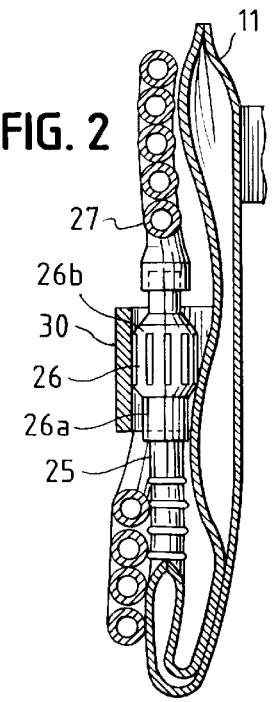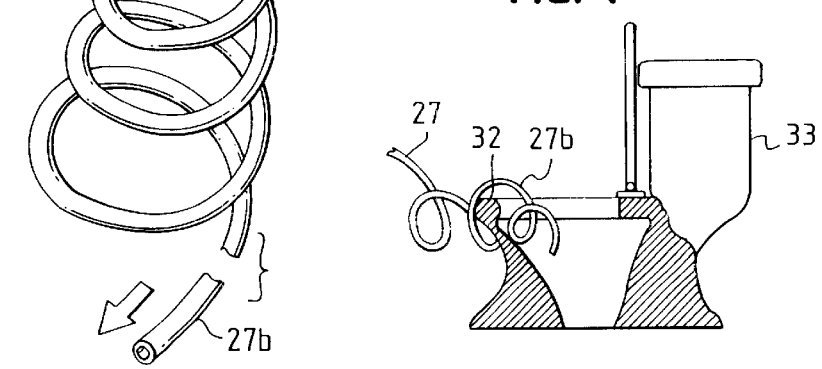

URINE BAG AND SELF-RETRACTING DRAIN TUBE THEREFOR

RELATED APPLICATIONS

This application is a continuation-in-part of application Ser. No. 09/229,799, filed Jan. 13, 1999 now U.S. Pat. No. 6,045,542.

BACKGROUND AND SUMMARY

Conventional urinary drainage bags are commonly strapped to a patient's leg above the knee, as disclosed in Barto U.S. Pat No. 3,897,785, so that urine will flow into the bag under the influence of gravity. For an ambulatory patient, such an arrangement is often inconvenient and uncomfortable because, as such a bag becomes filled with urine, there is a tendency for it to slide downwardly along the leg unless additional means are provided on the bag to restrain such sliding movement. Also, such leg bags may be conspicuous through clothing as the bags become filled and may be awkward to drain.

Cawood U.S. Pat. No. 4,449,971 discloses that gravity flow is not essential for purposes of filling a urine collection bag. Intrinsic bladder detrusor muscle tone and intraperitoneal pressures exerted upon the bladder of a catheterized ambulatory patient will cause urine to flow from the bladder to a level as high as 10 centimeters or more above the distal tip of the catheter. A highly effective urinary drainage system may therefore be provided for an ambulatory patient in which the collection bag is carried by a waistband or belt and is worn over the patient's abdomen instead of along the inside of the leg.

The bag disclosed in the Cawood patent has a short valve-equipped drain tube that extends downwardly from the bag when the contents are to be drained and that may be folded upwardly and inserted into a pocket provided by the bag when the drain tube is not in use. While such a drain tube may work satisfactorily for an ambulatory patient who is capable of standing with a urine collection bag positioned above a toilet bowl, and then manipulating the drain valve so that the contents of the bag may flow by gravity into the bowl, such a procedure may be difficult if not impossible for patients who are confined to wheelchairs. Such a patient must either try to stand—a manuever that may involve considerable risk—or must disconnect the bag from its waist strap (or unbuckle the waist strap) so that the bag may be held over the toilet bowl and drained.

A main aspect of this invention therefore lies in providing a urine collection bag of the type disclosed in U.S. Pat. No. 4,449,971 with an extendable and retractable drainage tube that allows the contents of such a bag to be drained into a toilet bowl even by a patient confined to a wheelchair and without first requiring removal of the bag by the patient. Specifically, the improvement takes the form of an elongated flexible plastic drainage tube that is in the shape of a flat coil, preferably of oval outline, and is connected or connectable to the valved drain port of the urine collection bag. The drain tube may be permanently attached to the port or, in a preferred embodiment, may be detachably joined to that port. The tube is of soft, flexible thermoplastic material and is thermoformed so that it is biased to assume its flattened coiled shape in the absence of forces applied to extend it. In its coiled condition, the drain tube lies flat against the front wall of the pouch and is held in that position by a retention strap which traverses the front wall of the pouch.

Another advantage of the present construction is that it facilitates use by patients with high urine volume output at night. The elongated drainage tube may be uncoiled and directed into a bedside receptacle, thus allowing a patient to wear an abdominal bag throughout the night without the risks of contamination that might arise if the abdominal bag and its catheter had to be removed and replaced by other drainage means for nighttime use. Similarly, the elongated drain tube allows a patient to wear an abdominal bag even while undergoing a surgical operation, since urine draining from the bag allows urine output to be monitored by an anesthesiologist. Upon completion of the operation, the drain tube may be disconnected from the bedside receptacle, allowed to return to its coiled condition, and replaced under the retaining strap of the abdominal bag, thus restoring the abdominal bag to its original condition for outpatient use.

Other features, objects, and advantages of the invention will become apparent from the specification and drawings.

DRAWINGS

FIG. 1 is a front elevational view of an abdominal bag equipped with the elongated drain tube of this invention.

FIG. 2 is an enlarged vertical sectional view taken along line 2—2 of FIG. 1.

FIG. 3 is a front elevational view similar to FIG. 1 but showing the drainage tube in partially uncoiled condition.

FIG. 4 is a diagramatic view illustrating how the coiled drainage tube may be hooked over the rim of a flush toilet.

DETAILED DESCRIPTION OF PREFERRED EMBODIMENTS

Referring to the drawings, the numeral 10 generally designates a urine collection device comprising an abdominal bag 11, a belt 12 for supporting the bag about a wearer's waist, and a catheter 13 for conveying urine from the bladder to the collection bag. In use, the bag would be worn as shown and described in aforementioned U.S. Pat. No. 4,449,971, the disclosure of which is incorporated by reference herein.

The bag 11 is substantially flat when empty and is dimensioned to extend over a patient's abdomen or belly. The front and rear walls 11a and 11b of the bag are joined together along their top, side and bottom edges 14, 15 and 16, respectively. Top edge 14 is generally straight and extends horizontally when the bag is worn. The walls of the bag may be formed of any suitable thermoplastic film that is tough, flexible, and liquid/gas impermeable. As indicated in the drawings, the edges 14–16 are preferably heat sealed together. The bottom edge 16 is generally V-shaped in outline with its side sections sloping downwardly toward the bag's vertical midline 17.

The bag may optionally include a soft, flexible rear panel (not shown) which may be of flocked or non-woven fabric. Such a rear panel, when provided, serves as a comfort panel to keep the bag from sticking to a patient's skin, and would preferably be joined to the rear wall 11b by the same peripheral heat seal extending along edges 14–16. Belt 12 may be secured to rear wall 11b by any suitable means. Where a rear comfort panel is provided, the strap portions 12a of the belt may extend outwardly through vertical slits (not shown) in the rear comfort panel, in which case direct attachment of the belt to the rear wall 11b becomes unnecessary since the rear comfort panel then serves to join the belt and bag together. Such a comfort panel is disclosed in copending application Ser. No. 09/299,799, filed Jan. 13, 1999, the disclosure of which is incorporated by reference herein.

An inlet tube 20 formed of polyvinyl chloride or other suitable thermoplastic material is heat sealed to the upper front wall 11a of the bag and communicates in the interior of the bag with a suitable one-way valve 21. As shown in FIG. 1, the exterior portion of the inlet tube is operatively connected to the proximal end 13a of catheter 13. The connection might be a permanent one, although a separable connection is preferred.

The one-way valve 21 may be formed of a pair of flexible thermoplastic strips heat sealed along their edges to define a passage communicating at one end with inlet tube 20 and open at its other end only when fluid pressure within the passage forces the strips apart, thereby functioning as an anti-refluxing flap valve as disclosed more fully in aforementioned U.S. Pat. No. 4,449,971.

A tubular drain port 25 equipped with valve 26 is heat sealed to the lower edges of the bag and communicates with the bag's interior. The particular valve depicted in the drawings is composed of two elements 26a and 26b that are threadedly connected to each other. Opening and closing of the valve is achieved simply by rotating element 26b one way or the other with respect to element 26a. Since such a valve is entirely conventional and well known for use in collection appliances, a more detailed description of its structure and operation is believed unnecessary.

The tubular drain port 25 is located along the bag's vertical midline as shown in FIGS. 1 and 2. A flexible self-retracting drain tube 27 has its proximal end connected to the valved drain port assembly 25, 26. The connection may be a permanent one but is preferably detachable, as by stretching the proximal end 27a over the outlet end of valve element 26b, since such detachability allows bag 11 to be used in the manner already described in the aforementioned U.S. Pat. No. 4,449,971 when the use of an elongated self-retracting drainage tube is deemed inconvenient or unnecessary.

The drain tube 27 is formed from a soft, flexible, thermoplastic material that may be thermoformed into a flat, coiled shape and will be biased to retain that shape, or retract into it, because of its elastic memory. Polyvinyl chloride is believed particularly effective, preferably of a durometer value on the Shore A scale of about 65 to 80, but other thermoplastic materials having similar properties may also be used. It has been found that if a PVC tube having an inside diameter of ¼ inches and a length of 30–36 inches is coiled into a flat spiral, preferably one of oval shape as shown in FIG. 1, and is then heated for approximately 15 minutes at a temperature of 200 to 225° F., the tubing when cooled will have acquired a "set" and will tend to return to its coiled configuration when it is extended and then released. Thus, the drainage tube may be easily extended for drainage of bag 11 as indicated in FIGS. 3 and 4 and, when the forces of extension are removed, the elastic memory will cause, or at least contribute, to self-retraction of the tube into the coiled configuration depicted in FIGS. 1 and 2. In that flat coiled shape, preferably with the long axis of the oval extending vertically when the bag is supported as shown in FIG. 1, the coiled tube may be folded upwardly against the front face 11a of bag 11.

Retention means are provided by the bag to hold the coiled tube 27 in its retracted condition. In the illustration given, the retention means takes the form of a flexible strap 30. The elongated strap extends transversely (horizontally) and includes central portion 30a and end portions 30b. Circular heat seals 31 not only join the end portions 30b to the front wall of the bag but also secure together the front and rear walls 11a and 11b at two laterally-spaced zones of attachment. It will be observed that the two spots or zones of interconnection are spaced equal distances on opposite sides of the vertical midline of the bag and that each heat seal 31 is located approximately midway between that midline and a side edge 15. The strap 30 is located so that when the drain tube 27 is coiled and folded upwardly into raised position the valve and the center of the flat coil will be at approximately the same elevation as the strap and can be easily tucked between front wall 11a and the central portion 30a of the strap (FIGS. 1 and 2).

As indicated in FIG. 3, the thermoformed drain tube 27 tends to retain its coiled condition even when its distal end 27b is pulled or extended outwardly away from the bag 11 during a draining procedure. That tendency to remain in coiled condition has been found useful in helping a user temporarily affix the distal end to a toilet bowl in preparing for a draining operation. FIG. 4 illustrates how the coils at the distal end 27b of drain tube 27 may be looped or hooked over the edge 32 of the bowl of a conventional flush toilet 33 by a patient seated in a wheelchair (not shown), thereby allowing the patient to use both hands in manipulating valve 26.

While in the foregoing, an embodiment of the invention has been described in detail for purposes of illustration, it will be understood by those skilled in the art that many of these details may be varied without departing from the spirit and scope of the invention.

What is claimed is:

1. A urine collection device comprising a flat bag adapted to be worn by a patient across the abdomen, said bag having front and rear walls of flexible thermoplastic joined to each other along top, bottom, and side edges to define a urine-receiving chamber; support means for supporting said bag from a patient's waist; a drain port located along said bottom edge and communicating with the interior of said bag; an inlet tube joined to said front wall above said drain port and adapted to be connected to a urethral catheter; and a one-way inlet valve communicating with said inlet tube for preventing flow in a reverse direction therethrough; wherein the improvement comprises an elongated flexible thermoplastic drain tube having first and second ends; said first end being connected to said drain port; said drain tube normally assuming a flat coiled condition and biased into said condition by the elastic memory of the thermoplastic from which said drain tube is formed; and retention means provided by said bag for holding said drain tube in flat coiled condition against the front wall of said bag.

2. The device of claim 1 in which said first end of said drain tube is detachably connected to said drain port.

3. The device of claims 1 or 2 in which said drain port is provided with manually operable valve means.

4. The device of claim 1 in which said drain tube when in flat coiled condition is oval in outline.

5. The device of claim 4 in which said oval has a long axis extending generally vertically when said bag is worn.

6. The device of claim 1 in which said retention means comprises a flexible strap traversing a mid section of said front wall of said bag; said strap having a central portion and a pair of opposite end portions; said end portions being secured to said front wall and said central portion extending over said drain tube and holding the same in coiled condition against the front wall of said bag.

* * * * *